United States Patent [19]

Frehel et al.

[11] 4,136,186
[45] Jan. 23, 1979

[54] THIENO[3,2-c]PYRIDINE DERIVATIVES

[75] Inventors: Daniel Frehel; Jean-Pierre Maffrand, both of Toulouse, France

[73] Assignee: Parcor, Paris, France

[21] Appl. No.: 763,876

[22] Filed: Jan. 13, 1977

[30] Foreign Application Priority Data

Jan. 22, 1976 [FR] France .................. 76 01637

[51] Int. Cl.² ............... C07D 513/04; A61K 31/44
[52] U.S. Cl. ........................... 424/256; 546/114;
546/298; 546/296; 546/299
[58] Field of Search ................. 260/294.8 C; 424/256

[56] References Cited

U.S. PATENT DOCUMENTS

| 4,051,141 | 9/1977 | Castaigne | 260/294.8 C |
| 4,075,215 | 2/1978 | Castaigne | 260/294.8 C |

Primary Examiner—Alan L. Rotman
Attorney, Agent, or Firm—Young & Thompson

[57] ABSTRACT

This invention relates to thieno[3,2-c]pyridine derivatives having the formula:

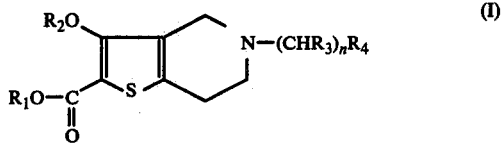

in which:
$R_1$ represents an alkyl radical having 1-6 carbon atoms;
$R_2$ represents a radical selected from hydrogen and an acyl group;
$R_3$ represents a radical selected from hydrogen; an acyl group; an alkoxycarbonyl group; a phenyl group; a phenyl group substituted with at least a substitutent selected with at least a substituent selected from halogen, hydroxy, nitro, amino, cyano, carboxy, alkoxycarbonyl, $C_{1-6}$ alkyl, $C_{1-6}$ alkoxy; a phenoxy group; a phenoxy group substituted with at least a substituent selected from halogen, hydroxy, nitro, amino, cyano, carboxy, alkoxycarbonyl, $C_{1-6}$ alkyl, and $C_{1-6}$ alkoxy; and a trifluoromethyl group;
$R_4$ represents hydrogen, an acyl group, an alkoxy carbonyl group, or a phenyl or phenoxy group optionally substituted with at least a halogen atom or a hydroxy, nitro, amino, cyano, carboxy, alkoxycarbonyl, $C_{1-6}$ alkyl, $C_{1-6}$ alkoxy group, or a trifluoromethyl group, and
n is an integer from 0 to 15; and their pharmaceutically acceptable acid addition salts.

Said derivatives have an inhibiting activity on blood-platelet aggregation, and anti-inflammator and sedative activities.

4 Claims, No Drawings

THIENO[3,2-c]PYRIDINE DERIVATIVES

This invention relates to new thieno[3,2-c]pyridine derivatives, to a process for their preparation and to their applications in human and veterinary medicine.

The new compounds of this invention have the following general formula:

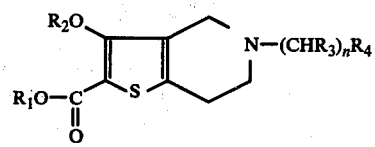

in which:
$R_1$ represents an alkyl radical having 1-6 carbon atoms;
$R_2$ represents hydrogen or an acyl group;
$R_3$ represents hydrogen or an alkyl group having 1-6 carbon atoms;
$R_4$ represents hydrogen, an acyl group, an alkoxy carbonyl group, or a phenyl or phenoxy group optionally substituted with at least a halogen atom or a hydroxy, nitro, amino, cyano, carboxy, alkoxycarbonyl, $C_{1-6}$ alkyl, $C_{1-6}$ alkoxy group, or a trifluoromethyl group, and
n is zero or an integer from 1 to 15.

The invention includes also within its scope the pharmaceutically acceptable acid solution salts of the compounds of the formula (I) with inorganic or organic acids. This invention relates also to a process for the preparation of compounds of the formula (I) as defined above, comprising reacting a piperidone derivative of the formula

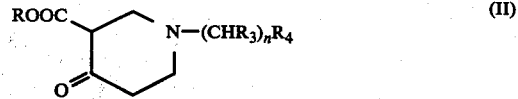

in which R represents a lower alkyl group and $R_3$, $R_4$ and n have the above-defined meanings, with a mercapto-acetic compound having the formula:

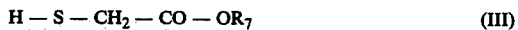

in which $R_7$ represents hydrogen or the symbol $R_1$ in a hydrochloric solution of an alcohol of the formula $R_1OH$ in which $R_1$ has the above-defined meaning, to give a derivative of the formula:

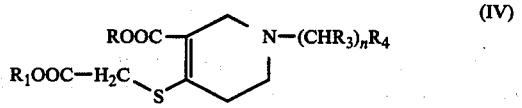

then cyclizing the derivative of the formula (IV) to give a derivative of the formula (I) in which $R_2$ is hydrogen and, if desired, acylating the latter derivative to give the corresponding derivative of the formula (I) in which $R_2$ is an acyl group.

The reaction of piperidone derivative (II) with mercaptoacetic compound (III) is preferably effected at room temperature while stirring the reaction mixture.

In the piperidone derivative of the formula (II) R is preferably methyl or ethyl.

The cyclization reaction of the compounds of the formula (IV) is preferably effected in the presence of a base such as sodium hydroxide, potassium hydroxide or potassium carbonate, in a solvent such as an alcohol of the formula $R_1OH$ or dimethyl formamide. This reaction leads to compounds of the formula (I) in which $R_2$ is hydrogen, which latter compounds may readily be converted to acylated derivatives ($R_2$ = acyl) by treatment with the corresponding acid anhydride or acid chloride.

The 4-piperidones of the formula (II) are known derivatives, the synthesis of which is described in the literature by: S. M. Mc. ELVAIN, J. Am. Chem. Soc., 1924, 46, 1721 S. M. Mc. ELVAIN & G. STORK, J. Am. Chem. Soc., 1946, 68, 1049 G. M. KUETTEL & S. M. Mc. ELVAIN, J. Am. Chem. Soc., 1931, 53, 2692 S. MOROSAWA, Bull. Chem. Soc. Japan, 1958, 31, 418.

The pyridine derivatives of the formula (IV) are new chemical compounds.

The salts of the compounds of the formula (I) may be prepared by methods well known to those skilled in the art.

The following non limiting Examples are given to illustrate the preparation of compounds of this invention.

EXAMPLE 1

Preparation of 5-o-Chlorobenzyl-2-ethoxycarbonyl-3-hydroxy-4,5,6,7-tetrahydro-thieno[3,2-c]pyridine (derivative n°1)

Procedure (a)

1-o-Chlorobenzyl-3-methoxycarbonyl-4-piperidone hydrochloride (63.6 g; 0.2 mole) is suspended in absolute ethanol (600 cc). The suspension is cooled to −10° C and a stream or dry hydrochloric gas is passed therethrough until the reaction medium becomes homogeneous. Ethyl mercapto-acetate (48 g; 0.4 mole) is then added thereto and hydrochloric gas is bubbled therethrough at −10° C during a further 4 hours.

The reaction mixture is then left aside at room temperature during 4 days, after which the solvent is evaporated in vacuo. The residue is made alkaline with a 5% sodium bicarbonate solution, neutralized with acetic acid and extracted with ether. The organic extracts are washed with water, dried over anhydrous sodium sulfate and evaporated, to give 1-o-chlorobenzyl-4-ethoxycarbonyl-methylthio-3-methoxycarbonyl-1,2,5,6-tetrahydro-pyridine of the formula (IV) as an oil which is converted to the oxalate which is recrystallized from isopropanol. M.p. = 162° C. Yield: 62 g (65%).

A solutiion of above free base (IV) (38.4 g; 0.1 mole) in 2N ethanolic potassium hydroxide solution (400 cc) is stirred during 10 hours at room temperature under a nitrogen atmosphere. The resulting heterogeneous mixture is concentrated in vacuo, made acidic with 2N hydrochloric acid, made alkaline with a 5% sodium bicarbonate solution and extracted with ether. The organic extracts are washed with water, dried over anhydrous sodium sulfate and evaporated to dryness. The resulting crystalline residue is recrystallized from cyclohexane, to give pale yellow crystals, M.p. = 106° C; Yield: 32.4 g (92%). Hydrochloride: white crystals, M.p. = 201° C (isopropanol).

Procedure (b)

A solution of 1-o-chlorobenzyl-3-methoxycarbonyl-4-piperidone hydrochloride (6 g; 0.019 mole) in absolute ethanol (150 cc) cooled to −10° C is saturated with dry hydrochloric gas. Mercaptoacetic acid (3.5 g; 0.038 mole) is added thereto and a slight stream of hydrochloric gas is passed therethrough at −10° C during 4 hours.

After setting the reaction mixture aside at room temperature during 90 hours, it is evaporated to dryness and the treatment is continued as described in procedure (a), to give 6.4 g (71%) of 1-o-chlorobenzyl-4-ethoxycarbonylmethylthio-3-methoxycarbonyl-1,2,5,6-tetrahydro-pyridine oxalate which may be cyclized as described in procedure (a) or as follows:

A mixture of compound of the formula (IV) (7.5 g; 0.019 mole), anhydrous potassium carbonate (3 g; 0.021 mole) and dimethyl formamide (50 cc) is stirred at room temperature during 12 hours. After filtering off the insoluble, the resulting material is poured over N hydrochloric acid (100 cc) and extracted with ether. The aqueous phase is made alkaline by addition of solid sodium bicarbonate and extracted with methylene chloride. The methylene chloride extracts are washed with water, dried over anhydrous sodium sulfate and evaporated to dryness. The residual yellowish crystals are recrystallized from cyclohexane: Yield, 5.6 g (83%).

EXAMPLE 2

Preparation of 5-benzoyl-2-ethoxycarbonyl-3-hydroxy-4,5,6,7-tetrahydro-thieno[3,2-c]pyridine (derivative n°2)

A solution of 1-benzoyl-3-methoxycarbonyl-4-piperidone (12 g; 0.046 mole) in absolute ethanol (150 cc), cooled to −10° C, is saturated with dry hydrochloric gas. Ethyl mercapto-acetate (10.8 g; 0.092 mole) is added thereto and a slight stream of hydrochloric gas is further passed therethrough at −10° C during 5 hours. After leaving the reaction mixture aside at room temperature during 70 hours, it is evaporated to dryness and the residue is dissolved in ether. The organic phase is washed with a 5% sodium bicarbonate solution and with water, dried over anhydrous sodium sulfate and concentrated in vacuo. The resulting 1-benzoyl-4-ethoxycarbonylmethylthio-3-methoxycarbonyl-1,2,5,6-tetrahydro-pyridine is obtained as an oil (Yield: 100%) and used directly in the next step:

A solution of the above product (4.9 g; 0.0135 mole) in 2N ethanolic potassium hydroxide (50 cc) is stirred at room temperature during 18 hours. The material is concentrated in vacuo, the residue is made acidic by addition of N hydrochloric acid and extracted with ether. The organic extracts are washed with water, dried over anhydrous sodium sulfate and evaporated to dryness. The resulting residue is crystallized from cyclohexane; M.p. = 145° C; Yield: 4.4 g (98%).

EXAMPLE 3

Preparation of 3-acetoxy-5-o-chlorobenzyl-2-ethoxycarbonyl-4,5,6,7-tetrahydro-thieno[3,2-c]pyridine (derivative n°3)

A solution of 5-o-chlorobenzyl-2-ethoxycarbonyl-3-hydroxy-4,5,6,7-tetrahydro-thieno[3,2-c]pyridine (35.3 g; 0.1 mole) in acetic anhydride (200 cc) is refluxed during one hour, under a nitrogen atmosphere. The reaction mixture is then evaporated to dryness and the residue is dissolved in ether. The organic phase is washed with water, dried over anhydrous sodium sulfate, treated with vegetable charcoal, filtered and evaporated in vacuo. The resulting pale yellow crystals are recrystallized from cyclohexane; M.p. = 110° C; Yield: 31.9 g (80%).

Derivative n°4

5-Benzyl-2-ethoxycarbonyl-3-hydroxy-4,5,6,7-tetrahydro-thieno[3,2-c]pyridine hydrochloride: white crystals, M.p. = 194° C (isopropanol), prepared according to procedure a) of Example 1. Cyclization yield: 78%.
Intermediate compound (IV): 1-benzyl-4-ethoxycarbonylmethylthio-3-methoxycarbonyl-1,2,5,6-tetrahydro-pyridine, oxalate: M.P. = 140° C (acetonitrile). Yield: 60%.

Derivative n°5

5-o-Chlorobenzyl-3-hydroxy-2-methoxycarbonyl-4,5,6,7-tetrahydro-thieno[3,2-c]pyridine White crystals, M.p. = 109° C (cyclohexane), prepared according to procedure a) of Example 1, using methanol as solvent in the various steps. Yield: 92%.
Intermediate compound (IV): 1-o-chlorobenzyl-4-methoxycarbonylmethylthio-3-methoxycarbonyl-1,2,5,6-tetrahydro-pyridine: oil, Yield: 72%.

Derivative n°6

2-Ethoxycarbonyl-3-hydroxy-5-methyl-4,5,6,7-tetrahydro-thieno[3,2-c]pyridine Orange crystals, M.p. = 71° C (dimethylformamide), prepared according to procedure a) of Example 1. Cyclization yield: 94%.
Intermediate compound (IV): 3-ethoxycarbonyl-4-ethoxycarbonylmethylthio-1-methyl-1,2,5,6-tetrahydro-pyridine, oxalate; M.P. = 172° C (ethanol). Yield: 65%.

Derivative n°7

2-Ethoxycarbonyl-3-hydroxy-4,5,6,7-tetrahydro-thieno[3,2-c]pyridine cream crystals, M.p. = 200° C (dimethylformamide), prepared according to procedure a) of Example 1. Yield: 96%. Intermediate compound (IV): 3-ethoxycarbonyl-4-ethoxycarbonylmethylthio-1,2,5,6-tetrahydro-pyridine, hydrochloride, M.p. = 166° C (ethanol). Yield: 70%.

Derivative n°8

3-Hydroxy-2-methoxycarbonyl-4,5,6,7-tetrahydro-thieno[3,2-c]pyridine beige crystals, M.P. = 190° C (dimethylformamide), prepared according to procedure a) of Example 1, using methanol as solvent in the various steps. Cyclization yield: 60%. Intermediate compound (IV): 3-ethoxycarbonyl-4-methoxycarbonylmethylthio-1,2,5,6-tetrahydro-pyridine, oil. Yield: 69%.

Derivative n°9

2-Ethoxycarbonyl-3-hydroxy-5-phenethyl-4,5,6,7-tetrahydro-thieno[3,2-c]pyridine orange crystals, M.p. = 84° C (cyclohexane), prepared according to procedure a) of Example 1. Cyclization yield: 91%. Intermediate compound (IV): 3-ethoxycarbonyl-4-ethoxycarbonylmethylthio-1-phenethyl-1,2,5,6-tetrahydro-pyridine, oxalate; M.p. = 148° C (ethanol). Yield: 73%.

Derivative n°10

2-Butoxycarbonyl-5-o-chlorobenzyl-3-hydroxy-4,5,6,7-tetrahydro-thieno[3,2-c]pyridine white crystals, M.p. = 93° C (cyclohexane), prepared according to procedure b) of Example 1. Cyclization yield: 60%. Intermediate compound (IV): 4-Butoxycarbonylmethylthio-1-o-chlorobenzyl-3-methoxycarbonyl-1,2,5,6-tetrahydro-pyridine, oil, Yield: 100%.

Derivative n°11

2,5-Diethoxycarbonyl-3-hydroxy-4,5,6,7-tetrahydrothieno[3,2-c]pyridine white crystals, M.p. = 88° C (cyclohexane), prepared according to the procedure of Example 2. Cyclization yield: 95%. Intermediate compound (IV): 1,3-Diethoxycarbonyl-4-ethoxycarbonylmethylthio-1,2,5,6-tetrahydro-pyridine: oil. Yield: 90%.

The results of pharmacological and toxicological tests reported below demonstrate the properties of the derivatives of the formula (I), particularly a low toxicity and an excellent tolerance, together with inhibiting activities on blood-platelet aggregation, anti-inflammatory and sedative activities. Thus, the invention relates to a therapeutic composition having in particular an inhibiting action on blood-platelet aggregation, anti-inflammatory and sedative activities comprising as active ingredient an efficient amount of a derivative of the formula (I) or a pharmaceutically acceptable acid addition salt thereof together with a pharmaceutically acceptable carrier or excipient.

I. TOXICOLOGICAL INVESTIGATION

The compounds of the formula (I) exhibit an excellent tolerance and a low toxicity. Thus, the $LD_{50}/24$ hrs/Kg body weight of the animal, determined in mice according to the method of Miller and Tainter, by the oral route, is in excess of 300 mg for all derivatives.

In addition, the tests carried out on acute, chronic, subchronic and delayed toxicity in various animal species evidenced no local or systemic reaction, no perturbation in the regularly effected biological control tests, no anomaly in the microscopic and macroscopic examinations carried out in the animals sacrificed and autopsied at the end of the experimentation.

II - PHARMACOLOGICAL INVESTIGATION (1°) Inhibiting action on blood-platelet aggregation A blood sample is taken from the jugular vein of rats of Wistar strain. From this citrated blood, and after centrifugation, is reconstituted a plasma containing 600,000 ± 20,000 platelets per $mm^3$ which will be used in all aggregation determinations.

(a) Determination of A.D.P.-induced blood-platelet aggregation 0.4 ml plasma is placed in a siliconized tube provided with a magnetic bar, which is also siliconized. The tube is introduced into an aggregometer connected with an optical density variation recorder. When light transmission has reached a stable value, 0.5 ml of a solution containing 10 μM A.D.P. (adenosine-diphosphate) are introduced in the tube. Blood-platelet aggregation then induces an increase of light transmission followed by a decrease subsequent to the deaggregation phase.

The thus determined maximum variation of optical density characterizes the intensity of the aggregation.

(b) Determination of collagen-induced blood-platelet aggregation

The A.D.P. solution is substituted with a collagen solution (bovine tendon extract).

(c) Results

Different groups of 20 rats are used, each group being administered orally a test derivative, at a dosage of 100 mg/kg.

The results obtained in the course of tests a) and b) are tabulated in following Table I which indicates the percent inhibition of blood-platelet aggregation obtained, with respect to the control, 3 hours after treatment.

TABLE I

| Test compound | Percent inhibition | |
|---|---|---|
| | A.D.P. | Collagen |
| Derivative n°1 | 61.2 | 90.2 |
| Derivative n°2 | 62.8 | 94.6 |
| Derivative n°3 | 62.4 | 92.9 |
| Derivative n°4 | 64.8 | 95.2 |
| Derivative n°5 | 64.4 | 96.7 |
| Derivative n°6 | 63.8 | 93.2 |
| Derivative n°7 | 62.5 | 95.6 |
| Derivative n°8 | 62.1 | 94.3 |
| Derivative n°9 | 64.5 | 93.8 |
| Derivative n°10 | 63.6 | 90.2 |
| Derivative n°11 | 62.1 | 91.00 |

(1°) Anti-inflammatory action (a) Localised carrageenin-induced edema method:

A 1% carrageenin solution (0.1 ml) is injected in the metatarsal flexor muscles of the right hind limb of rats at time 0. The animals of the treated group are additionally administered orally 100 mg/kg of the test derivative, respectively one hour prior to and then simultaneously with the phlogogenic agent, and then one hour and 2.5 hours thereafter. The percent antiinflammatory activity, as a function of time, is determined with respect to the control group by measurements effected with a ROCH micrometer at times 0, one hour, two hours, three hours and five hours after carrageenin administration.

The results obtained are tabulated in following Table II:

TABLE II

| Derivative n° | Percent anti-inflammatory activity | | | |
|---|---|---|---|---|
| | after 1 hour | after 2 hours | after 3 hours | after 5 hours |
| 1 | 46 | 53 | 56 | 60 |
| 2 | 42 | 48 | 50 | 53 |
| 3 | 38 | 45 | 49 | 51 |
| 4 | 39 | 45 | 50 | 53 |
| 5 | 41 | 47 | 51 | 55 |
| 6 | 34 | 40 | 43 | 48 |
| 7 | 36 | 41 | 45 | 52 |
| 8 | 43 | 49 | 53 | 55 |
| 9 | 42 | 46 | 50 | 54 |
| 10 | 37 | 42 | 48 | 51 |
| 11 | 40 | 46 | 49 | 53 |

(b) Ovalbumin-induced systemic edema method

Rats are administered a simultaneous intraperitoneal injection of 1 ml ovalbumin and 0.5 ml of a 1% aqueous Evans Blue solution. The animals of the treated group are additionally administered orally 100 mg/kg of the test derivative, one hour prior to and simultaneously with said ovalbumin administration. The intensity of the phenomenon thus induced is scored according to a scale from 1 to 5, according to the progress of the inflammatory syndrome. Thus are determined with respect to the control group the mean intensity and the percent decrease of the edema reaction, as a function of time.

The percent anti-inflammatory activity obtained 2 hours and 3 hours, respectively, after ovalbumin injection, is tabulated in following Table III:

TABLE III

| Derivative n° | Percent anti-inflammatory activity | |
|---|---|---|
| | after 2 hours | after 3 hours |
| 1 | 54 | 63 |
| 2 | 49 | 58 |
| 3 | 51 | 59 |
| 4 | 48 | 56 |
| 5 | 47 | 55 |
| 6 | 52 | 59 |
| 7 | 50 | 60 |
| 8 | 48 | 57 |
| 9 | 53 | 62 |
| 10 | 50 | 59 |
| 11 | 51 | 61 |

(3°) Sedative action

Experimentation provided evidence of the sedative effect of the compounds of the formula (I). Thus study was conducted according to the method disclosed by Samuel Irwin (PH. D. Animal and Clinical Pharmacology Technics in Drug Evaluation).

The test derivatives are administered by gastric tubing in a single dose of 50 mg/kg to mice.

Observation of their behavior and the study of the different physiological parameters recorded (temperature, cardiac and respiratory frequency) evidence in all animals a marked decrease of the motor activity and the muscular tone, together with a decrease of the alertness and of the reactions to noise and to the environment.

In addition, the compounds of the formula (I) potentiate very markedly the effect of hypnotics. Indeed, on oral administration to different groups of mice, at a dosage of 50 mg/kg, thirty minutes prior to intraperitoneal injection of an infrahypnotic dosage of sodium pentobarbital, they produce, with respect to the untreated reference animals, a marked potentiation of the barbiturate.

The results obtained are tabulated in following Table IV.

TABLE IV

| Test derivative | percent animals put to sleep | average falling-asleep time | average sleeping time |
|---|---|---|---|
| None (reference group) | 0 | 0 | 0 |
| Derivative n°1 | 60 | 9 mn 15 s | 1 hr 45 mn |
| Derivative n°2 | 60 | 7 mn 20 s | 1 hr 28 mn |
| Derivative n°3 | 80 | 9 mn 25 s | 1 hr 33 mn |
| Derivative n°4 | 70 | 8 mn 40 s | 1 hr 36 mn |
| Derivative n°5 | 70 | 7 mn 45 s | 1 hr 40 mn |
| Derivative n°6 | 90 | 8 mn 30 s | 1 hr 57 mn |
| Derivative n°7 | 90 | 9 mn 00 s | 1 hr 52 mn |
| Derivative n°8 | 80 | 7 mn 50 s | 1 hr 35 mn |
| Derivative n°9 | 100 | 8 mn 10 s | 1 hr 52 mn |
| Derivative n°10 | 90 | 8 mn 30 s | 1 hr 45 mn |
| Derivative n°11 | 60 | 7 mn 50 s | 1 hr 34 mn |

The results of such investigations provide evidence of the low toxicity and of the interesting inhibiting properties on blood-platelet aggregation of the derivatives of the formula (I), together with their anti-inflammatory and sedative properties, which make them highly useful in human and veterinary medicine.

The therapeutic composition of this invention may be formulated for oral administration as tablets, coated tablets, capsules, drops and syrups. It may also be formulated for rectal administration as suppositories, and, for parenteral administration, as injectable solutions.

Each unit dose contains advantageously from 0.010 g to 0.300 g active ingredient, the daily dosage regimen varying within a range from 0.010 g to 0.900 g active ingredient, according to the age of the patient and the disease to be treated.

Non-limiting examples of pharmaceutical formulations of the therapeutic composition of this invention are given below:

| | |
|---|---|
| Example 12 - Tablets | |
| Derivative n°1 | 0.100 g |
| Excipient: polyvinylpyrrolidone, corn starch, magnesium stearate, talc | |
| Example 13 - Coated tablets | |
| Derivative n°4 | 0.075 g |
| Excipient: silicic acid, sugar, lactose, talc, magnesium stearate, kaolin, shellac, rosin, starch, sugar, tartrazine yellow | |
| Example 14 - Capsules | |
| Derivative n°7 | 0.125 g |
| Excipient: magnesium stearate, talc | |
| EXAMPLE 15 - Injectable ampoules | |
| Derivative n°8 | 0.100 g |
| Excipient: isotonic solvent, sufficient amount to make | 3 ml |
| EXAMPLE 16 - Suppositories | |
| Derivative n°10 | 0.080 g |

Excipient: Semi-synthetic triglycerides

The toxocological and pharmacological investigations reported above demonstrate the good tolerance of the derivatives of the formula (I) together with their inhibiting properties on blood-platelet aggregation, and their anti-inflammatory and sedative activities.

Thus, the therapeutic composition of this invention may be beneficially administered to humans, for preventive or curative purposes, in the treatment of diseases inducing a pathological change of blood-platelet aggregation, such as the thromboembolic diseases.

It may also be administered in the treatment of all inflammatory conditions, whatever their etiology: chronic inflammatory rheumatism, degenerative rheumatism, abarticular conditions, inflammatory conditions of the oto-rhino-laryngologic area, in traumatology and in post-operative surgery.

In addition, due to its sedative properties, it is usefully prescribed in the treatment of symptoms reflecting an exaggerated nervous excitability, such as emotivity, nervousness, anxiety, irritability, insomnia, migraines, headaches, cardiac erethism, climacteric neuro-vegetative disorders, and disorders due to hypertension.

Having now described our invention what We claim as new and desire to secure by Letters Patent is:

1. A thieno[3,2-c]pyridine derivative selected from a compound having the formula:

$$R_2O-\overset{\displaystyle\phantom{C}}{\underset{\displaystyle R_1O-\overset{\|}{\underset{O}{C}}}{\diagdown}} \text{(thieno[3,2-c]pyridine ring)}-N-(CHR_3)_nR_4$$

in which:

$R_1$ is alkyl having 1-6 carbon atoms;
$R_2$ is hydrogen;
$R_3$ is hydrogen;
$R_4$ is a radical selected from hydrogen, benzoyl, phenyl, and phenyl substituted with a halogen atom; and
n is an integer from 0 to 2; and a pharmaceutically acceptable acid addition salt thereof.

2. Therapeutic composition having an inhibiting activity on blood-platelet aggregation, comprising, as active ingredient, a therapeutically effective amount of a compound as claimed in claim 1, together with a therapeutically acceptable carrier.

3. Therapeutic composition having antiinflammatory activity, comprising, as active ingredient, a therapeutically effective amount of a compound as claimed in claim 1, together with a therapeutically acceptable carrier.

4. Therapeutic composition having sedative activity, comprising, as active ingredient, a therapeutically effective amount of a compound as claimed in claim 1, together with a therapeutically acceptable carrier.

* * * * *